US006844458B2

(12) United States Patent
Copeland et al.

(10) Patent No.: US 6,844,458 B2
(45) Date of Patent: *Jan. 18, 2005

(54) VEGETABLE OIL REFINING (75) Inventors: Dick Copeland, Omaha, NE (US); W. Maurice Belcher, Omaha, NE (US)

(73) Assignee: IP Holdings, L.L.C., Omaha, NE (US)

(*) Notice: Subject to any disclaimer, the term of this patent is extended or adjusted under 35 U.S.C. 154(b) by 0 days.

This patent is subject to a terminal disclaimer.

(21) Appl. No.: 10/190,263

(22) Filed: Jul. 3, 2002

(65) Prior Publication Data

US 2003/0050492 A1 Mar. 13, 2003

Related U.S. Application Data (60) Continuation-in-part of application No. 09/776,477, filed on Feb. 2, 2001, now Pat. No. 6,441,209, which is a continuation-in-part of application No. 09/550,375, filed on Apr. 14, 2000, now abandoned, which is a division of application No. 09/197,953, filed on Nov. 20, 1998, now Pat. No. 6,172,248.

(51) Int. Cl.$^7$ ................................................. C11B 3/00
(52) U.S. Cl. .................... 554/212; 554/175; 554/190
(58) Field of Search ................................. 554/190, 101, 554/201, 212, 175

(56) References Cited

U.S. PATENT DOCUMENTS

| | | |
|---|---|---|
| 2,349,270 A | 5/1944 | Hickman |
| 2,410,926 A | 11/1946 | Bush et al. |
| 3,153,055 A | 10/1964 | Brown et al. |
| 4,036,865 A | 7/1977 | Hartmann et al. |
| 4,049,686 A | 9/1977 | Ringers et al. |
| 4,072,482 A | 2/1978 | Aoki et al. |
| 4,240,972 A | * 12/1980 | Mag et al. .................. 260/424 |
| 4,698,185 A | 10/1987 | Dijkstra et al. |
| 4,996,072 A | 2/1991 | Marschner et al. |
| 5,138,075 A | 8/1992 | Ohgaki et al. |
| 5,239,096 A | 8/1993 | Rohdenburg et al. |
| 5,487,817 A | 1/1996 | Fizet |
| 5,696,278 A | 12/1997 | Segers |
| 6,172,248 B1 * | 1/2001 | Copeland et al. ........... 554/190 |

FOREIGN PATENT DOCUMENTS

| | | |
|---|---|---|
| EP | 0 348 004 | 12/1989 |
| EP | 0 507 363 | 10/1992 |
| FR | 2753200 | 3/1998 |
| GB | 701631 | 12/1953 |
| GB | 701633 | 12/1953 |
| GB | 714160 | 8/1954 |
| GB | 1 118 373 | 7/1968 |
| LU | 60116 | 12/1969 |
| NL | 18441 | 8/1928 |
| WO | WO 86/04603 | 8/1986 |
| WO | WO 94/12596 | 6/1994 |
| WO | WO 96/41852 | 12/1996 |

OTHER PUBLICATIONS

Chem. Abstr., 124:235513, 1996.*
Chem. Abstr., 94:155202, 1981.*
Patent Abstract of Japan, vol. 1997, No. 10, Oct. 31, 1997, JP 09 154504 (Asahi Denka Kogyo KK), Jun. 17, 1997.
Erickson, David R., *Degumming and Lecithin Processing and Utilization*, in Practical Handbook of Soybean Processing and Utilization, pp. 1–38, 56–64, 174–202, 239–257, 297–313 (David R. Erickson ed. 1995).

(List continued on next page.)

*Primary Examiner*—Deborah D. Carr
(74) *Attorney, Agent, or Firm*—McDonnell Boehnen Hulbert & Berghoff LLP (57) ABSTRACT

The present invention relates to improved methods for refining vegetable oils. Vegetable oil is combined with organic acid and subjected to high shear to finely disperse the acid solution in the oil. The resulting acid-and-oil mixture is mixed at low shear for a time sufficient to sequester contaminants into a hydrated impurities phase, producing a purified vegetable oil phase.

13 Claims, 4 Drawing Sheets

OTHER PUBLICATIONS

J. C. Schmidt and F.T. Orthoefer, *Modified Lecithins*, in LECITHINS 203, 206 (Bernard F. Szuhaj & Gary R. List eds., 1985).

Van Nieuwenhuyzen, W., Lecithin Production and Properties, *J. Amer. Oil Chem. Soc.* 53:425 (1976).

Chemical Abstract 124:235513, 1996.

Chemical Abstract 94:155202, 1981.

Data Base WPI, Section Ch Week 197543, Derwent Publication Ltd., London, GB, AN 1975–71933W, XP002204395.

Data Base WPI, Section Ch Week 198901, Derwent Publication Ltd., London, GB, AN 1989–003045, XP002033366.

Pan, L.G., Campana, A. Tomas, M.C., and Anon, M.C., , *J. Amer. Oil Chem. Soc*, vol. 77, No. 12, 2000, pp. 1273–1276.

* cited by examiner

VEGETABLE OIL REFINING

This is a continuation-in-part of application Ser. No. 09/776,477, filed Feb. 2, 2001 which is a continuation-in-part of Ser. No. 09/550,375 filed Apr. 14, 2000 abandoned, which is a divisional of Ser. No. 09/197,953, filed Nov. 20, 1998.

FIELD OF THE INVENTION

This invention relates to improved methods for refining vegetable oils and byproducts thereof. More particularly, this invention relates to improved processes for producing vegetable oils having reduced content of impurities such as free fatty acids and phosphatides.

BACKGROUND OF THE INVENTION

Organic Acid Refining

Vegetable oils are typically obtained by pressing or extracting the oil seeds of plants such as corn or soybeans. Properly processed vegetable oils are suitable for use in many edible oil and fat compositions destined for human consumption. Such edible oils and fats include salad oils, cooking oils, frying fats, baking shortenings, and margerines. In addition to being widely used in edible oils and fats, vegetable oils are also increasingly utilized in important industrial products such as caulking compounds, disinfectants, fungicides, printing inks, and plasticizers.

Vegetable oils primarily consist of triglycerides, but several other compounds are also present. Some of these additional compounds, such as diglycerides, tocopherols, sterols, and sterol esters, need not necessarily be removed during processing. Other compounds and impurities such as phosphatides, free fatty acids, odiferous volatiles, colorants, waxes, and metal compounds negatively affect taste, smell, appearance and storage stability of the refined oil, and hence must be removed. Carefully separated, however, some of these additional compounds, particularly the phosphatides, are valuable raw materials. It is therefore important to select a vegetable oil purifying method that maximizes removal of impurities but does so in a way that least impacts the compounds removed.

Vegetable oil impurities are typically removed in four distinct steps of degumming, refining, bleaching, and deodorizing. Of these four steps, degumming removes the largest amount of impurities, the bulk of which are hydratable phosphatides. Refining primarily removes non-hydratable phosphatides, soaps created from the neutralization of free fatty acids, and other impurities such as metals. Bleaching then improves the color and flavor of refined oil by decomposing peroxides and removing oxidation products, trace phosphatides, and trace soaps. Soybean oil bleaching materials include neutral earth (commonly termed natural clay or fuller's earth), acid-activated earth, activated carbon, and silicates. Deodorizing is the final processing step and prepares the oil for use as an ingredient in many edible products including salad oils, cooking oils, frying fats, baking shortenings, and margerines. The deodorizing process generally comprises passing steam through refined oil at high temperature and under near vacuum conditions to vaporize and carry away objectionable volatile components.

Vegetable oil refining, also known as neutralization or deacidification, essentially involves removing free fatty acids (FFA) and phosphatides from the vegetable oil. Most refining operations employ either alkali refining (also termed caustic refining) or physical refining (also termed steam refining). Of these two refining methods, alkali refining predominates.

For either refining method, an optional but preferred first step is a conventional water degumming process. Degumming refers to the process of removing hydratable phosphatides and other impurities such as metals from vegetable oils. Crude vegetable oils contain both hydratable phosphatides (HPs) and non-hydratable phosphatides (NHPs). A simple degumming process comprises admixing soft water with the vegetable oil and separating the resulting mixture into an oil component and an oil-insoluble hydrated phosphatides component (frequently referred to as a "wet gum" or "wet lecithin"). The NHPs, generally considered to be calcium and magnesium salts of phosphatidic acids, are largely unaffected by water and remain soluble in the oil component.

Normally, refiners also must introduce chelating agents following degumming processes to remove metal compounds from crude vegetable oil, which typically contains calcium, potassium, magnesium, aluminum, iron and copper. Left in place, these metal impurities form salts of phosphatidic acid, thereby contributing to the NHP content. Moreover, metal contaminants, especially iron, can darken oil during deodorization, and even small amounts of iron that do not affect the oil's color can nevertheless dramatically reduce stability of refined oil.

Treating crude vegetable oil with soft water produces a degummed oil and a phosphatide concentrate containing the hydratable phosphatide fraction. This phosphatide concentrate subsequently can be removed from the degummed oil by a convenient method such as centrifugal separation. Phosphatide concentrates coming from centrifugal separation will generally contain up to about fifty percent by weight water, and typically will contain from about twenty-five to about thirty percent by weight water. In order to minimize chances of microbial contamination, phosphatide concentrates must be dried or otherwise treated immediately. Dried phosphatide concentrates can be profitably sold as commercial lecithin. Degummed oil is further refined to remove NHPs and other unwanted compounds.

Mineral acid also is sometimes added during the water degumming process to help minimize the NHP content of degummed oil. The acid combines with calcium and magnesium salts, enabling phosphatidic acids to migrate from the oil to the water phase, thus eliminating them from the crude oil. However, using mineral acid during degumming is inappropriate when seeking to recover gums intended for use as lecithin because the presence of mineral acid will cause darkening of the lecithin.

In alkali refining, free fatty acids and gums are removed from crude or degummed oil by mixing the oil with a hot, aqueous alkali solution, producing a mixture of so-called neutral oil and soapstock (also termed refining byproduct lipid), which is an alkaline mixture of saponified free fatty acids and gums. The neutral oil is then separated from the soapstock, typically by centrifugation. The soapstock has commerical value due to its fatty acid content but must be processed further in order to render it salable. The neutral oil is further processed to remove residual soap.

Soapstock is treated in a process called acidulation, which involves breaking or splitting the soap into separate oil and aqueous phases through addition of a mineral acid such as sulfuric acid to reduce the pH to approximately 1.5, followed by thorough heating and mixing. Because the aqueous phase is heavier than the oil phase, the acidulated soapstock is separated from the oil by gravity or centrifugation. The separated oil (termed acid oil) has essentially the composition of the neutral oil and is drawn off, washed with water to completely remove mineral acid and sludge, and sold, usually as an animal feed supplement. The remaining aqueous phase (termed acid water) is the final waste product and can either be used in other processes or neutralized before being discarded.

The alkali refining process has several drawbacks, however, mainly related to soapstock formation. One drawback is refining losses that occur due to the soapstock's emulsifying effect, wherein soapstock acts to take up a portion of the valuable neutral oil into the aqueous soapstock solution. To minimize such emulsification losses, the crude or degummed oil is usually heated to between 158° F. and 194° F. prior to being contacted with the hot alkali solution. However, heating will not completely prevent emulsions from forming, nor will it entirely break emulsions once formed. Centrifugation forces also are insufficient to completely break emulsions of neutral oil in soapstock.

Another drawback to alkali refining is losses that occur when a portion of the neutral oil undergoes alkaline hydrolysis, often referred to as saponification, to produce undesirable fatty acid salts. Allowing the alkali solution and the crude or degummed oil to remain in contact for only short times can minimize saponification losses but is often insufficient to remove impurities other than fatty acids, especially impurities such as phosphatides and metal compounds. Consequently, short contact times can make it necessary to conduct a second round of refining.

Yet another alkali refining drawback is that raw soapstock is troublesome to handle. Soapstock solidifies quickly upon cooling, so heated holding tanks and transfer lines are required to maintain temperatures above 140° F. Elevated temperatures also are required to prevent fermentation. On the other hand, overly heating soapstock causes it to boil, producing excessive and troublesome foaming.

Still another drawback is the difficulty in disposing of the acid water created during soapstock splitting. Acid water is high in biochemical oxygen demand (BOD) and low in pH. Disposal regulations require at minimum that the acid water be neutralized before the waste can be dumped. Many states have much more stringent pollution controls, requiring often costly solutions to ensure effluent biodegradability.

Thus, alkali refining involves many processing steps and has many drawbacks. In attempting to address the problems associated with alkali refining, operators must simultaneously vary many factors including the amount of heat applied, the amount and concentration of alkali, and retention times. Successfully balancing all these factors is a complex and difficult task. Furthermore, successful balancing of factors nevertheless can leave the need for additional refining cycles.

An alternative to alkali refining is physical refining. Physical refining is a steam distillation process essentially the same as that used in conventional vegetable oil deodorization processes, where steam passing through vegetable oil vaporizes and carries away free fatty acids. The main advantage of physical refining over alkali refining is that no soapstock is generated. A second advantage is lower refining losses because there is no saponification of oil and no oil emulsifaction by soapstock.

Accordingly, there is significant interest in physical refining due to its economic advantages and friendliness compared to alkali refining. But because physical refining does not remove NHPs, any oils to be physically refined must be free of NHPs in order to ensure stable refined oils. Oils such as palm oil and tallow, which have low NHP content, can be successfully physically refined. But oils such as soybean oil and sunflower seed oil, which are relatively high in NHPs, are not commonly physically refined because the pre-refining step of water degumming does not remove NHPs. Moreover, physically refined soybean oils have only limited acceptance in the U.S. market due to their lack of flavor stability.

Thus, although present methods exist for refining vegetable oils, significant drawbacks remain. Alkali refining can substantially remove phosphatides and other impurities but presents economic challenges and water pollution concerns. Physical refining is economically and environmentally less challenging, but many vegetable oils including soybean oil which are high in NHPs cannot be acceptably physically refined. Consequently, there is a need for an improved process for purifying vegetable oils, and especially soybean oil.

A prior method for refining vegetable oils is disclosed in U.S. Pat. No. 2,410,926 comprising mixing strong aqueous acid solutions with oils, adding filter aid material to absorb the aqueous phase, and separating purified oil from the residue. Typically, 1.5 to 2 percent by weight of a saturated aqueous organic acid solution is added to crude vegetable oil. The amount of water is kept low and is limited to the amount that can be absorbed by the filter aid. Solid acids are used so that any excess above the solubility limit of the small amount of water employed will be retained in the filter cake, and will not pass with the refined oil. A disadvantage of this method is the need to filter out absorbent before the oil can be used.

U.S. Pat. No. 4,698,185 describes a vegetable oil refining method comprising the steps of finely dispersing an aqueous organic acid in a water-degummed oil to form an acid-in-oil dispersion, allowing the phases to remain in contact for a time sufficient to decompose metal salts of phosphatidic acid, adding a base to the acid-in-oil dispersion to increase pH to above 2.5 without substantial formation of soap, and finally separating the dispersion into an oil phase and an aqueous phase containing the phosphatides. The method typically utilizes 0.4 to 2 percent by weight of a 20 to 60 percent by weight organic acid solution and requires a degree of dispersion of at least 10 million droplets of aqueous acid per gram of oil. A disadvantage of this method is that pH basic materials like those used in alkali refining must be added in order to remove NHPs.

A somewhat similar method disclosed in U.S. Pat. No. 4,240,972 comprises adding an acid to a heated stream of crude vegetable oil and then immediately passing the mixture through a static mixer, intensively mixing for a fraction of a second to produce an acid-in-oil dispersion having acid droplets smaller than 10 microns, and then separating the dispersion into an oil phase and an aqueous phase containing the phosphatides. This method claims that producing ultrafine acid droplets eliminates the need for lengthy acid-oil contact times. However, acid-oil contact times of less than about 15 minutes are generally insufficient to sequester substantial amounts of metal impurities.

U.S. Pat. No. 4,049,686 describes a method of removing phosphatides from vegetable oils comprising dispersing an aqueous solution of an acid or acid anhydride into a heated vegetable oil, chilling the mixture to a temperature below 104° F., adding a small amount of additional water, allowing the phases to remain in contact for a time sufficient to decompose metal salts of phosphatidic acid, and separating the dispersion into an oil phase and an aqueous phase containing the phosphatides. This method claims that by cooling to a temperature below 104° F. and adding water in a step separate from the aqueous acid addition, the phosphatides are converted into a semi-crystalline phase. Disadvantages of this method include the need to add aqueous acid and water in separate steps and the need for a chilling step, both being aspects that increase overall processing complexity.

Further improvements in purifying vegetable oil have been sought, particularly with regard to obtaining purified vegetable oil low in free fatty acids, phosphatides, and other impurities such as metals in an environmentally friendly manner. The present invention relates to an improved process having advantages over those previously disclosed. In particular, this invention relates to a non-alkali process for purifying vegetable oil employing a dilute aqueous organic acid solution. This invention also relates to purified vegetable oil obtained by the improved process.

Lecithin Deodorizing

The term lecithin, from a true chemical sense, refers to phosphatidyl choline. However, as used by commercial suppliers, the term lecithin refers to a product derived from vegetable oils, especially soybean oil. In addition to phosphatidyl choline, lecithin derived from vegetable oil includes phosphatidyl ethanolamine, phosphatidyl inositol, phosphatidic acid, phosphatidyl serine, cyclolipids, and other components such as free sugars, metals and free fatty acids. Because they contain several phosphatidyl derivatives, commercial lecithins are often referred to as phosphatides or phosphatide concentrates. Other synonymous terms for phosphatide concentrates include wet gums or wet lecithin.

Lecithins are utilized in a broad variety of applications and perform an array of valuable functions. In edible compositions, lecithin contributes nutritional value and also can act as an emulsifying agent, surface active agent, anti-spattering-agent, or stabilizing agent. Lecithin can be used in technical applications as an anti-foam agent, dispersing agent, wetting agent, stabilizing agent, and as an anti-knock compound for gasoline formulations. In particular, in foods such as baked goods or margarine, lecithin is used as a dispersing agent, emulsifier, viscosity reducer and antioxidant. In cosmetics such as shampoos or skin lotions, lecithin is employed as a foam stabilizer, emollient, emulsifier, and wetting agent. In pharmaceuticals targeted for either topical or parenteral administration, lecithin functions as softening agent, carrier, emulsifier, and penetration enhancer. Lecithin also possesses unique release properties, and is useful in pan frying and pan grease formulations for baking, as well as in mold release formulations enabling casting forms to be easily removed.

However, lecithin can have an objectionable odor and flavor that is difficult to remove. Phosphatides easily oxidize when subjected to heating, and such oxidative products can contribute a bitter or rancid taste to lecithin. Heating of phosphatides can also induce formation of volatile decomposition products such as 4,5-dimethylisoxazole, which contributes an objectionable flavor to lecithin. Other volatile compounds such as isophorone, a contributor of objectionable odor, can form by an aldol condensation reaction involving solvent remaining from crude vegetable oil refining processes.

Decomposition rate, oxidation rate, and reaction rate all increase with increasing temperature. Furthermore, once objectionable volatile compounds are formed, high temperature conditions can cause chemical bonding of these compounds to the lecithin. These factors urge processing lecithin at low temperatures. Yet the desire to discourage microbial growth by minimizing lecithin's water content urges drying at high temperatures to ensure maximum moisture removal. Thus, there are conflicting considerations in lecithin processing and a need for a process that resolves these competing factors and produces optimal lecithin.

A prior method for preparing phosphatide concentrates is disclosed in U.S. Pat. No. 4,713,155 comprising treating crude vegetable oil with a hydrating agent, separating the resulting wet gum from the remaining oil by centrifuging, treating the separated wet gum in an electromagnetic field of 40,000–240,000 A/m, and drying the phosphatide concentrate at 122° F. to 158° F. under atmospheric pressure (760 mm Hg). This process is said to allow greater reduction in percent by weight moisture than earlier methods similarly operating at atmospheric pressure but not employing an electromagnetic field treatment step. A disadvantage of this method is that complicated equipment is necessary in order to reliably and safely deliver the required strength of electromagnetic field.

More conventional processes for removing moisture from phosphatide concentrates involve drying at high temperature under reduced pressure. Commercial lecithin is typically produced in a continuous process by drying phosphatide concentrates at a temperature of from 176° F. to 203° F. and at an absolute pressure of from about 50 mm Hg to about 300 mm Hg. Erickson, David R., *Degumming and Lecithin Processing and Utilization,* in Practical Handbook of Soybean Processing and Utilization 174, 179–80 (David R. Erickson ed. 1995); Van Nieuwenhuyzen, W., *J. Amer. Oil Chem. Soc.* 53:425 (1976). However, as noted above, processing lecithin at high temperatures risks increasing the concentration of objectionable volatile compounds, and further risks permanently fixing these objectionable compounds to the lecithin via chemical bonding.

Further improvements in processing lecithin have been sought, particularly with regard to obtaining lecithin having improved odor and flavor characteristics via reduced content of objectionable volatile compounds. The present invention relates to an improved process having advantages over those previously disclosed. In particular, this invention relates to a process for removing objectionable volatile components from lecithin using a combination of stripping steam and drying at low pressure and moderately elevated temperature. This invention also relates to lecithin obtained by the improved process.

Vegetable Oil Deodorizing

Deodorization is usually the final step in producing edible vegetable oils and fats. Vegetable oils such as soybean oil typically contain volatile impurities that can impart objectionable odor and taste. These volatile compounds must be removed in amounts sufficient to produce deodorized oil having consumer-preferred characteristics. Impurities imparting objectionable properties to vegetable oil include free fatty acids, aldehydes, ketones, alcohols, hydrocarbons, tocopherols, sterols, and phytosterols. Following removal, some of these impurities, especially tocopherols, can be recovered and profitably sold.

Vegetable oil deodorization typically involves a steam stripping process wherein steam is contacted with vegetable oil in a distillation apparatus operating at low pressure and a temperature sufficient to vaporize objectionable volatile impurities at the operating pressure. This process, commonly known as vacuum-steam deodorization, relies upon volatility differences between the vegetable oil and the objectionable impurities to strip the relatively more volatile objectionable impurities from the relatively less volatile vegetable oil. Vacuum-steam deodorization treatment also beneficially decomposes peroxides in the vegetable oil and removes other volatile compounds that may result from such decomposition.

In a typical vacuum-steam deodorizing process, vegetable oil is introduced into a distillation apparatus having a plurality of vertically spaced trays, commonly termed stripping trays. Within each stripping tray, steam injected into the vegetable oil entrains objectionable volatile impurities. The combined steam and entrained distillation vapors are then condensed into a distillate that can be disposed of or processed further to recover valuable materials. Condensation of distillation vapors, like those produced during deodorization, is generally accomplished under vacuum. The deodorized vegetable oil is subsequently cooled and is available for sale or further processing.

Vegetable oil consists of triglycerides composed mainly of three unsaturated fatty acids—oleic, linoleic, and linolenic—esterified on a glycerol molecule in various combinations. Fatty acids in cis form predominate in vegetable oil; however, these fatty acids can convert into trans form under the influence of heating. Edible fats and oils containing trans fatty acids present health concerns and are therefore undesirable.

Vegetable oil also contains tocopherols in amounts that vary depending on the plant from which the vegetable oil was extracted. Soybean oil in particular contains roughly 0.10 to 0.20 percent by weight tocopherols in mixed $\beta$, $\gamma$, $\delta$ and $\epsilon$ isomeric forms. These tocopherol isomers all demonstrate antioxidant properties in varying degrees and hence are valuable raw materials. Tocopherols are high boiling, however, and generally only vaporize at temperatures above about 500° F. at pressures of about 10 mm Hg or less.

Steam temperature and the time for which the steam contacts the vegetable oil are both important variables directly influencing the types and amounts of objectionable volatile impurities that can be removed in a vacuum-steam deodorizing process. Increasing temperature more rapidly removes objectionable volatile impurities and tocopherols, but also produces more undesirable reactions such as trans fatty acid formation, fat splitting, and polymerization. Decreasing temperature reduces the rate of undesirable reactions such as trans fatty acid formation, but also removes less of the tocopherols and reduces deodorizer throughput capacity by requiring longer contact times. In addition to steam temperature, other variables influencing contact time include the amount of steam used relative to the vegetable oil, the quality of the vegetable oil, and the type of equipment used. Deodorizers utilizing typical steam sparger designs and operating at a uniform temperature of about 450° F. to 510° F. and a pressure of about 6 mm Hg. will usually require a 45 to 60 minute holding time.

Seeking maximum tocopherol recovery urges deodorizing at relatively high temperatures. Yet a desire to avoid trans fatty acid formation urges deodorizing at relatively lower temperatures and/or minimizing the time for which the oil experiences high temperature, which can lead to insufficient removal of objectionable volatile impurities. Accordingly, there is significant interest in a method of deodorizing vegetable oil that maximizes tocopherol recovery and removal of objectionable volatile impurities yet minimizes trans fatty acid formation.

A prior method for deodorizing vegetable oils is disclosed in U.S. Pat. No. 4,072,482 comprising passing superheated steam through oil located in a deodorizing tray of a continuous deodorizing apparatus operating at a temperature of 500° F. and a pressure of from 2 to 6 mm Hg. Multiple deodorizing trays can be used, each operating at 500° F. and each contacting steam with oil for a time of from 10 to 60 minutes. Operating at 500° F., this process would be expected to remove significant amounts of tocopherol but at the same time produce deodorized oil containing a relatively high amount of trans fatty acids.

Further improvements in deodorizing vegetable oils have been sought, particularly with regard to obtaining deodorized vegetable oil low in trans fatty acids and low in tocopherol. The present invention relates to an improved process for deodorizing vegetable oils having advantages over those previously disclosed. This invention also relates to deodorized vegetable oil obtained by the improved process.

SUMMARY OF THE INVENTION

One aspect of the present invention relates to an improved process for refining vegetable oil using organic acid. An improved organic acid refining process of the present invention effectively removes phosphatides, and other impurities such as metals from crude or degummed vegetable oil in an environmentally friendly way. The improved organic acid refining process of the invention also minimizes the risk of degrading the removed impurities, some of which are valuable raw materials.

One object of this aspect of the invention is to provide an organic acid refining process that produces refined vegetable oil having improved odor, flavor, and storage stability, and characterized by a reduced content of free fatty acids, phosphatides, and other impurities such as metals.

Another object of this aspect of the invention is to provide an improved process for refining vegetable oil that combines vegetable oil with a dilute aqueous organic acid solution at high shear to form an acid-and-oil mixture and then mixes the acid-and-oil mixture at low shear to sequester contaminants into a hydrated impurities phase and produces a purified vegetable oil phase.

Still another object of this aspect of the invention is to provide refined vegetable oil prepared according to the improved process.

Yet another object of this aspect of the invention is to provide a hydrated impurities phase prepared according to the improved process comprising a phosphatide concentrate which is a hydrolyzed lecithin.

One embodiment of this aspect of the invention is a process for refining vegetable oil comprising admixing a dilute aqueous organic acid solution with a heated stream of crude vegetable oil to give an acid-oil blend; subjecting the acid-oil blend to high shear for a time sufficient to finely disperse the dilute aqueous organic acid solution in the crude vegetable oil and give an acid-and-oil mixture; and mixing the acid-and-oil mixture for a time sufficient to sequester contaminants into a hydrated impurities phase and produce a purified vegetable oil phase.

Another embodiment of this aspect of the invention is a process for refining vegetable oil comprising admixing a dilute aqueous organic acid solution with a heated stream of crude vegetable oil to give an acid-oil blend; subjecting the acid-oil blend to high shear for a time sufficient to finely disperse the dilute aqueous organic acid solution in the crude vegetable oil and give an acid-and-oil mixture; mixing the acid-and-oil mixture for a time sufficient to sequester contaminants into a hydrated impurities phase and produce a purified vegetable oil phase; and separating the hydrated impurities phase and the purified vegetable oil phase.

Yet another embodiment of this aspect of the invention is a refined vegetable oil wherein phosphatides and other impurities such as metals have been removed from the vegetable oil by the improved organic acid refining process of the invention.

A still further embodiment of this aspect of the invention is a hydrated impurities phase removed from the vegetable oil and comprising a hydrolyzed lecithin.

Another aspect of the present invention relates to an improved process for removing objectionable volatile components from lecithin. An improved lecithin deodorizing process of the present invention effectively removes objectionable volatile components while drying phosphatide concentrates. The improved lecithin deodorizing process of the invention also minimizes both the risk of heat damage to the phosphatides and the danger of chemically fixing objectionable volatile compounds to the lecithin.

One object of this aspect of the invention is to provide a process for treating phosphatide concentrates which produces lecithin having improved odor and flavor characterized by a reduced content of objectionable volatile compounds.

Another object of this aspect of the invention is to provide an improved process for removing objectionable volatile components from lecithin by contacting the phosphatide concentrate with stripping steam during drying at low pressure and moderately elevated temperature.

Still another object of this aspect of the invention is to provide an improved process for removing objectionable volatile components from lecithin by contacting the lecithin with steam during drying.

A further object of this aspect of the invention is to provide lecithin prepared according to the improved process.

One embodiment of this aspect of the invention is a lecithin deodorizing process comprising introducing a phosphatide concentrate into a dryer utilizing an operating pressure of less than about 50 mm Hg and a drying temperature sufficient to vaporize water and the objectionable volatile components at the operating pressure; drying the phosphatide concentrate for a time sufficient to convert the phosphatide concentrate into a dried lecithin containing no more than about 0.5 percent by weight water and a vaporized byproduct containing the objectionable volatile components; and discharging the dried lecithin from the dryer at a temperature of from about 120° F. to about 140° F.

Another embodiment of this aspect of the invention is a lecithin deodorizing process comprising introducing a phosphatide concentrate into a dryer utilizing an operating pressure of less than about 10 mm Hg and a drying temperature sufficient to vaporize water and the objectionable volatile components at the operating pressure; injecting steam into the dryer and contacting the steam with the phosphatide concentrate; drying the phosphatide concentrate for a time sufficient to convert the phosphatide concentrate into a dried lecithin containing no more than about 0.5 percent by weight water and a vaporized byproduct containing the objectionable volatile components; and discharging the dried lecithin from the dryer at a temperature of from about 120° F. to about 140° F.

Yet another embodiment of this aspect of the invention is a deodorized lecithin wherein objectionable volatile components have been removed by the improved lecithin deodorizing process of the invention.

A still further aspect of the present invention relates to an improved process for deodorizing vegetable oil. An improved vegetable oil deodorizing process of the present invention removes objectionable volatile impurities while minimizing trans fatty acid conversion. The improved vegetable oil deodorizing process also maximizes recovery of valuable impurities such as tocopherols.

One object of this aspect of the invention is to provide a process for deodorizing vegetable oil that produces deodorized vegetable oil having improved odor, flavor, and storage stability, and characterized by a reduced content of objectionable volatile impurities.

Another object of this aspect of the invention is to provide an improved process for deodorizing vegetable oil that produces low trans fatty acid formation.

Still another object of this aspect of the invention is to provide an improved process for deodorizing vegetable oil that enables maximizing recovery of valuable impurities such as tocopherols.

A still further object of this aspect of the invention is to provide deodorized vegetable oil prepared according to the improved process.

One embodiment of this aspect of the invention is a process for deodorizing vegetable oil comprising introducing vegetable oil containing objectionable volatile impurities into a first tray of a deodorizer having at least two trays and operating at a pressure of less than about 10 mm Hg., the first tray operating at a temperature of from about 500° F. to about 525° F.; contacting the vegetable oil in the first tray with steam to vaporize a substantial fraction of the objectionable volatile impurities into a first vapor phase, leaving a liquid residue containing a remaining portion of objectionable volatile impurities; introducing the liquid residue into a second tray of the deodorizer operating at a temperature of from about 435° F. to about 465° F.; contacting the liquid residue in the second tray with steam to vaporize a substantial fraction of the remaining portion of objectionable volatile impurities into a second vapor phase, leaving a deodorized vegetable oil; and recovering the deodorized vegetable oil.

One embodiment of this aspect of the invention is a process for deodorizing vegetable oil comprising introducing vegetable oil containing objectionable volatile impurities into a first tray of a deodorizer having at least two trays and operating at a pressure of less than about 10 mm Hg., the first tray operating at a temperature of from about 500° F. to about 525° F.; contacting the vegetable oil in the first tray with steam to vaporize a substantial fraction of the objectionable volatile impurities into a first vapor phase, leaving a liquid residue containing a remaining portion of objectionable volatile impurities; introducing the liquid residue into a second tray of the deodorizer operating at a temperature of from about 435° F. to about 465° F.; contacting the liquid residue in the second tray with steam to vaporize a substantial fraction of the remaining portion of objectionable volatile impurities into a second vapor phase, leaving a deodorized vegetable oil; recovering the deodorized vegetable oil; and cooling the deodorized vegetable oil.

One embodiment of this aspect of the invention is a process for deodorizing vegetable oil comprising introducing vegetable oil containing objectionable volatile impurities into a first tray of a deodorizer having at least two trays and operating at a pressure of less than about 10 mm Hg., the first tray operating at a temperature of from about 500° F. to about 525° F.; contacting the vegetable oil in the first tray with steam to vaporize a substantial fraction of the objectionable volatile impurities into a first vapor phase, leaving a liquid residue containing a remaining portion of objectionable volatile impurities; introducing the liquid residue into a second tray of the deodorizer operating at a temperature of from about 435° F. to about 465° F.; contacting the liquid residue in the second tray with steam to vaporize a substantial fraction of the remaining portion of objectionable volatile impurities into a second vapor phase, leaving a deodorized vegetable oil; recovering the deodorized vegetable oil; cooling the deodorized vegetable oil; and combining and condensing the first vapor phase and the second vapor phase to form a distillate.

A still further embodiment of this aspect of the invention is a deodorized vegetable oil from which objectionable volatile impurities have been removed by the improved vegetable oil deodorizing process of the invention.

These and other objects of the invention will become apparent in light of the detailed description below.

DESCRIPTION OF A PREFERRED EMBODIMENT

Organic Acid Refining

Figure 1:
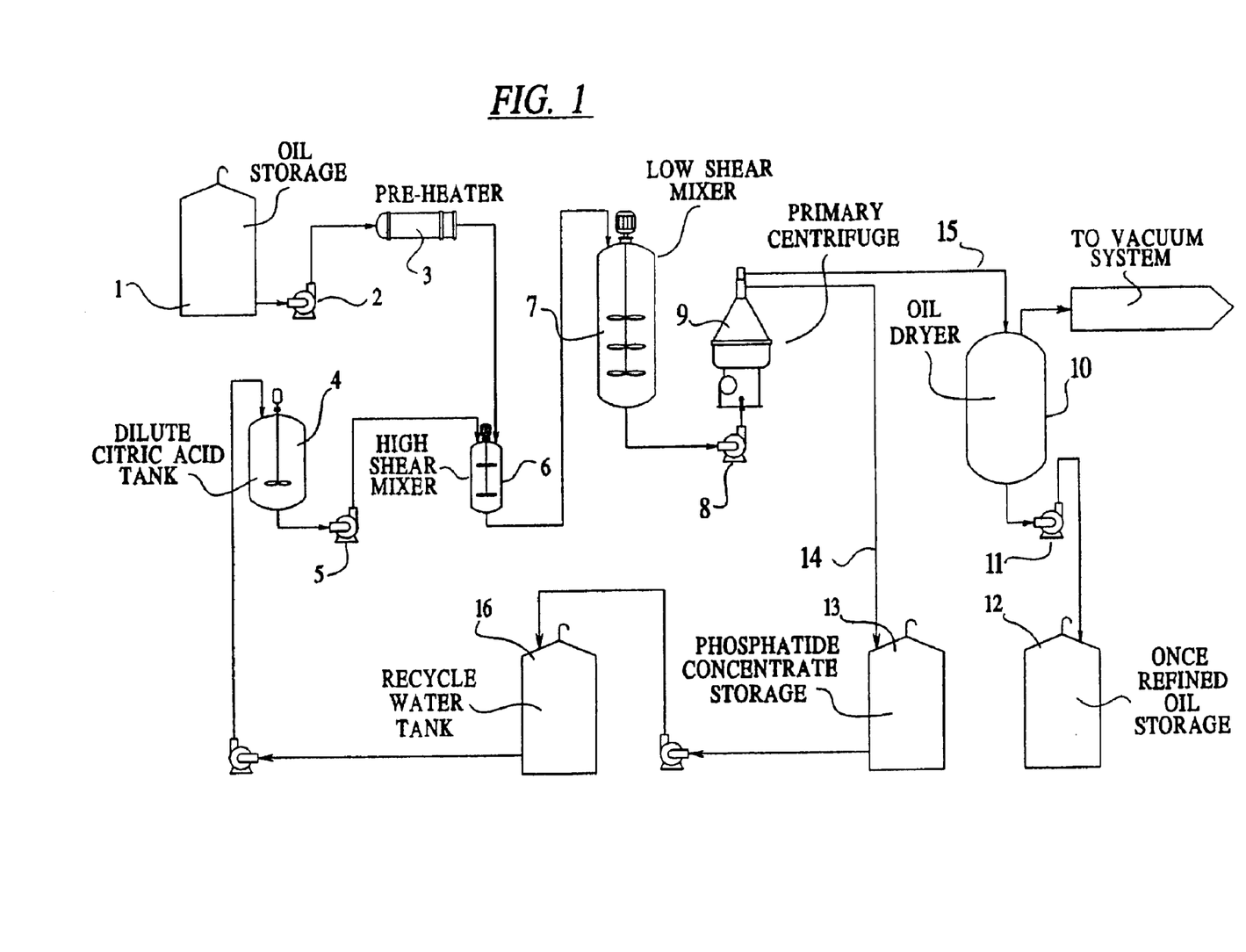
FIG. 1 is a process flow scheme suitable for carrying out the improved vegetable oil refining process of the invention.

The improved process for purifying vegetable oils can be conducted as a batch or a continuous process. As illustrated in FIG. 1, crude or degummed vegetable oil is supplied from a storage tank 1 through pump 2 to a pre-heater 3 wherein the vegetable oil is heated to a temperature of from about 190° F. to about 220° F. Suitable vegetable oils include but are not limited to those derived from soybean oil, corn oil, cottonseed oil, palm oil, peanut oil, rapeseed oil, safflower oil, sunflower seed oil, sesame seed oil, rice bran oil, coconut oil, canola oil, and mixtures thereof. A particularly preferred vegetable oil is soybean oil.

The vegetable oil to be purified can be either crude or "degummed" oil. Degumming refers to the process of removing hydratable phosphatides from crude vegetable oils during refining. Crude vegetable oils contain both hydratable and non-hydratable phosphatides. A simple degumming process comprises admixing water with the vegetable oil and separating the resulting mixture into an oil component and an oil-insoluble hydrated phosphatides component (frequently referred to as a "wet gum" or "wet lecithin"). Non-hydratable phosphatides, generally considered to be calcium and magnesium salts of phosphatidic acids, are largely unaffected by water and remain soluble in the oil component. Treating crude vegetable oil with water thus produces a phosphatide concentrate containing the hydratable phosphatide fraction and a degummed oil containing the non-hydratable phosphatide fraction. This degummed oil can be removed from the phosphatide concentrate by a convenient method such as centrifugal separation.

The vegetable oil is heated in pre-heater 3 to a temperature of from about 190° F. to about 220° F., preferably from about 195° F. to about 215° F., and most preferably from about 200° F. to about 210° F., depending on the source from which the vegetable oil was derived. Heating the vegetable oil minimizes the potential for losses due to emulsification when the oil is later contacted with an aqueous phase. Heating the vegetable oil also produces preferred handling viscosities and facilitates later mixing steps. Pre-heater 3 can be constructed according to many designs and can impart heat directly or indirectly to the vegetable oil. A preferred pre-heater 3 is a shell and tube heat exchanger available from Doyle & Roth and having an overall heat transfer coefficient of 170 BTU/h/ft$^2$/° F.

The heated vegetable oil is introduced into high shear mixer 6 wherein it is combined with a dilute aqueous organic acid solution supplied from a source 4 via pump 5, thereby producing an acid-oil blend. When the present invention is carried out as a batch process, the heated vegetable oil and the dilute aqueous organic acid solution can be introduced sequentially or simultaneously and in any order into high shear mixer 6. When the present invention is carried out as a continuous process, the heated vegetable oil and the dilute aqueous organic acid solution are introduced simultaneously into high shear mixer 6. The dilute aqueous organic acid solution optionally can be heated prior to its addition into high shear mixer 6.

The dilute aqueous organic acid solution may be prepared from any food grade organic acid, including but not limited to phosphoric acid, acetic acid, citric acid, tartaric acid, succinic acid, or combinations thereof. A particularly preferred organic acid is citric acid. Using a food grade organic acid, as opposed to a mineral acid, ensures that phosphatides removed during the purifying process can be purified and sold as commercial lecithin to the food industry. Using an organic acid also enables sequestering metal contaminants without the need to add other chelating agents.

The dilute aqueous organic acid solution can be prepared by dissolving an appropriate amount of a solid organic acid in water, or it can be prepared by further diluting a previously prepared aqueous organic acid solution of greater strength. In preparing the dilute aqueous organic acid solution, demineralized water is preferably used. Using demineralized water avoids the possibility of converting hydratable phosphatides to non-hydratable phosphatides. As used herein, the term demineralized water means water substantially devoid of calcium and magnesium ions.

The dilute aqueous organic acid solution has a concentration based on the combined weight of organic acid and water of from about 1 to about 5 percent by weight, preferably from about 2 to about 4 percent by weight, and most preferably from about 2 to about 3.5 percent by weight. The dilute aqueous organic solution is combined with the heated vegetable oil in a ratio of from about 3:97 to about 20:80, preferably from about 5:95 to about 15:85, and most preferably from about 8:92 to about 12:88, depending on the source from which the vegetable oil is derived and on whether the vegetable oil has been degummed.

The acid-oil blend is mixed at high shear in the high shear mixer 6 for a time sufficient to finely disperse the dilute aqueous organic acid solution in the vegetable oil and give an acid-and-oil mixture. Generally, the acid-oil blend is mixed for a time of less than about 30 seconds, preferably less than about 15 seconds, and most preferably less than about 5 seconds. Mixing parameters are selected according to the mechanical design of the high shear mixer. Important mixer design criteria include the ratio of tank height to tank diameter, the ratio of impeller diameter to tank diameter, and the number and positioning of individual blades on the impeller. A preferred high shear mixer 6 is a High Shear Mixer MX100 available from Alfa Laval and having a tank height to tank diameter ratio of about 4:1. Preferably, high shear mixer 6 employs 5 impellers, 2 of which are radial flow impellers and 3 of which are axial flow impellers, disposed along a mixing shaft connected to a motor generating from about 30 to about 40 horsepower.

High shear as used herein means mixer design criteria and impeller operating conditions combining to produce flow velocities of at least about 45 feet per second. High shear mixing according to the invention generally requires at least one impeller rotating at a speed of from about 900 to about 1500 rpm and having a blade tip speed of from about 4000 to about 9000 ft/min, thereby generating high shear flow velocities of at least about 45 feet per second.

The acid-and-oil mixture is pumped to a low shear mixer 7 wherein it is mixed at low shear for a time sufficient to sequester contaminants into a hydrated impurities phase and produce a purified vegetable oil phase. Generally, the mixing design criteria requiring consideration in producing low shear are the same as those discussed above in the context of producing high shear. A preferred low shear mixer 6 is a 250 or 500 gallon Retention Mixer available from Alfa Laval and having a tank height to tank diameter ratio of about 4:1. Preferably, low shear mixer 7 employs from about 40 to about 60 axial flow impellers disposed along a mixing shaft connected to a motor generating from about 5 to about 7.5 horsepower.

Low shear as used herein means mixer design criteria and impeller operating conditions combining to produce flow velocities of less than about 20 feet per second. Preferably, low shear mixing of the acid-and-oil mixture occurs with at least one impeller rotating at a speed of from about 68 to about 600 rpm and having a blade tip speed of from about 600 to about 950 ft/min, thereby generating low shear flow velocities of less than about 20 feet per second.

The acid-and-oil mixture is mixed at low shear for a time of less than about 16 minutes to allow sequestering of contaminants, especially metals, into the hydrated impurities phase. The acid-and-oil mixture is preferably mixed at low shear mixing for a time of from about 6 to about 14 minutes, and most preferably from about 8 to about 12 minutes. The term sequestering as used herein refers to the process wherein contaminants are either directly or indirectly (through chemical conversion into water-soluble forms) taken up into the hydrated impurities phase.

Following low shear mixing, the combined hydrated impurities and purified vegetable oil phases are advantageously pumped to a centrifuge 9 via pump 8 wherein the two phases undergo centrifugal separation and exit in separate physical streams 14 and 15. A preferred centrifuge 9 is a PX 90 available from Alfa Laval.

The hydrated impurities stream 14 is sent to a holding vessel 13 and stored for subsequent processing into commercial lecithin. Water can be separated from the hydrated impurities stream and can be recycled without other treatment for use in earlier steps of the organic acid refining process. Because water can be recycled without the need for additional and expensive treatment, such as neutralization, the organic acid refining process of the invention generates substantially no discharge water. The purified vegetable oil stream 15 is sent to dryer 10 operating at less than atmospheric pressure and an elevated temperature sufficient to vaporize any residual water or objectionable volatile components at the operating pressure. A preferred dryer 10 is a Votator Thin Film Dryer available from L.C.I. Corp. Preferably, dryer 10 operates at a temperature of from about 160° F. to about 190° F. and at a vacuum of about 21 to about 29 feet of water, operating conditions which effectively remove residual water. The dried purified vegetable oil is then sent to holding vessel 12 via pump 11 and stored for subsequent use or sale.

The hydrated impurities phase produced by the organic acid refining process of the invention is a phosphatide concentrate commonly termed wet lecithin. Surprisingly, however, the phosphatide concentrate produced by the organic acid refining process of the invention is a hydrolyzed lecithin containing at least about 5 percent by weight combined lyso and monoacyl forms of glyceryl phospholipids and containing a ratio of hydratable phosphatides to non-hydratable phosphatides in a ratio of at least about 9:1.

Obtaining a hydrolyzed lecithin directly from a crude vegetable oil is a novel and unexpected benefit provided by the improved organic acid refining process of the invention. According to known processes, hydrolyzed lecithin is normally obtained either via acidic or basic hydrolysis or via enzymatic action. A typical acidic hydrolysis process for producing hydrolyzed lecithin comprises multiple processing steps of adding water and an acid such as hydrochloric acid to a dried lecithin, subsequently neutralizing with a base such as sodium hydroxide, and then redrying the lecithin. J. C. Schmidt and F. T. Orthoefer, *Modified Lecithins,* in LECITHINS 203, 206 (Bernard F. Szuhaj & Gary R. List eds., 1985). A typical enzymatic process for producing hydrolyzed lecithin comprises adding costly animal-derived or synthetic enzymes to a wet lecithin to catalyze conversion of the lecithin into a hydrolyzed lecithin. Moreover, enzymatic processes for producing hydrolyzed lecithin require that the enzymes be filtered out after lecithin conversion, adding further expense. Thus, previously known methods for obtaining hydrolyzed lecithin have required complex and expensive processing steps. Surprisingly, the organic acid refining process of the invention produces hydrolyzed lecithin directly and simply from a phosphatide-containing vegetable oil without the need for subsequent and expensive processing.

Lecithin Deodorizing

Figure 2:
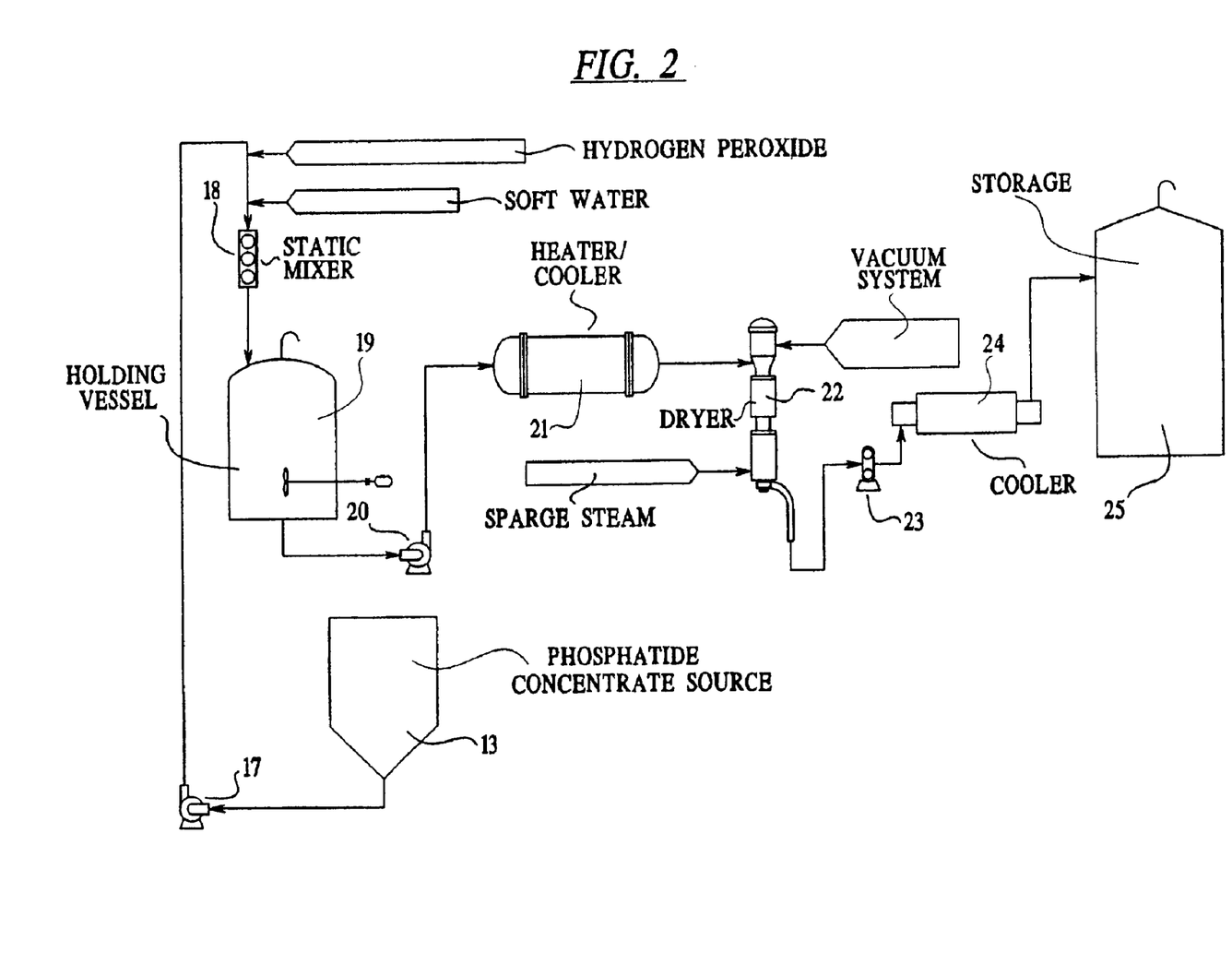
FIG. 2 is a process flow scheme suitable for carrying out the improved lecithin deodorizing process of the invention.

As illustrated in FIG. 2, the improved lecithin deodorizing process of the present invention begins by withdrawing a phosphatide concentrate from a source. Suitable phosphatide concentrates include but are not limited to those derived from vegetable oils such as soybean oil, corn oil, cottonseed oil, palm oil, peanut oil, rapeseed oil, safflower oil, sunflower seed oil, sesame seed oil, rice bran oil, coconut oil, canola oil, and mixtures thereof. Particularly preferred are phosphatide concentrates derived from soybean oil.

One convenient source of phosphatide concentrates results from "degumming" of vegetable oils. Degumming refers to the process of removing hydratable phosphatides from vegetable oils. Crude vegetable oils contain both hydratable and non-hydratable phosphatides. A simple degumming process comprises admixing demineralized water with the vegetable oil and separating the resulting mixture into an oil component and an oil-insoluble hydrated phosphatides component (frequently referred to as a "wet gum" or "wet lecithin"). Non-hydratable phosphatides are largely unaffected by demineralized water and remain soluble in the oil component. Treating crude vegetable oil with demineralized water thus produces a phosphatide concentrate comprising the hydratable phosphatide fraction. This phosphatide concentrate subsequently can be removed from the remaining oil by a convenient method such as centrifugal separation. Phosphatide concentrates coming from centrifugal separation will generally contain up to about fifty percent by weight water, and typically will contain from about twenty-five to about thirty percent by weight water. In order to minimize chances of microbial contamination, phosphatide concentrates must be dried or otherwise treated immediately.

In the improved lecithin deodorizing process of the invention, a phosphatide concentrate is supplied from a source 13 through pump 17, past which $H_2O_2$ and demineralized water are combined with the phosphatide concentrate. The $H_2O_2$ can also be added in the hydration tank as an alternative. Adding $H_2O_2$ as a bleaching agent helps improve the odor and flavor of the final product. The $H_2O_2$ is preferably added as a 0.2 percent by weight aqueous solution. The $H_2O_2$ is used in an amount of from about 0.1 to about 0.3 percent by weight of phosphatide concentrate, preferably from about 0.1 to about 0.2 percent by weight of phosphatide concentrate, and most preferably from about 0.1 to about 0.15 percent by weight of phosphatide concentrate, depending on the quality of the vegetable oil from which the phosphatide concentrate was derived.

Adding demineralized water further dilutes the phosphatide concentrate and improves the release of volatile compounds during drying. As used herein, the term demineralized water means water substantially devoid of calcium and magnesium ions. Non-hydratable phosphatides are generally considered to be calcium and magnesium soaps of phosphatidic acids. Thus, using demineralized water avoids the possibility of converting hydratable phosphatides into non-hydratable phosphatides. Demineralized water is added in an amount of from about 1 to about 3 percent by weight of phosphatide concentrate, preferably from about 1 to about 2.5 percent by weight of phosphatide concentrate, and most preferably from about 1 to about 2 percent by weight of phosphatide concentrate, depending on the quality of the vegetable oil from which the phosphatide concentrate was derived.

The combined phosphatide concentrate, $H_2O_2$, and demineralized water are passed through a static mixer 18, which thoroughly mixes them to form a phosphatide concentrate containing about 35 percent by weight water. Static mixers are tubular structures having fixed interior mixing elements which simultaneously divide flow and provide high intensity radial mixing. Such mixers are commercially available under the tradenames Kenics Static Mixer, Komax Motionless Blender, Lightnin Series 50 In-Line Blender, Ross Motionless Mixer, and Sulzer Static Mixer. A particularly preferred static mixer is a Kenics Static Mixer available from Chemineer providing a flow velocity of generally at least about 14 feet per second.

The phosphatide concentrate is pumped into a holding vessel 19, then pumped to a heat exchanger 21 via pump 20. Heat exchanger 21 heats the phosphatide concentrate to a temperature of from about 120° F. to about 140° F. This temperature may vary somewhat depending on the composition of the phosphatide concentrate, but preferred handling viscosities occur above a temperature of about 120° F. On the other hand, due to the danger of inducing heat damage to the phosphatides and the danger of chemically fixing objectionable volatile compounds to the lecithin, it is preferred not to exceed a temperature of about 150° F. Preferably, the phosphatide concentrate is heated to a temperature of from about 120° F. to about 150° F. Most preferably, the phosphatide concentrate is heated to a temperature of from about 120° F. to about 140° F.

The heated phosphatide concentrate is then pumped to a dryer 22. Either a batch-type or a continuous drying process will suffice, but continuous drying is preferred. More preferred is a continuous agitated-film dryer. Most preferably, dryer 22 is a thin-film dryer such as a Votator Turba Film available from L.C.I. Corp.

Drying parameters are crucial in producing lecithin having consumer-preferred odor and flavor. The phosphatide concentrate having a content of about 35 percent by weight water preferably must be dried down to less than about 0.5 percent by weight water. In order to minimize inducing heat damage to the phosphatides and the danger of chemically fixing objectionable volatile compounds to the lecithin, it is preferred not to exceed a temperature of about 150° F. Even at this temperature, it is preferred to minimize the amount of time the phosphatide concentrate experiences elevated temperature. For these reasons, drying under reduced pressure is preferred.

Reduced pressure can be generated by any convenient source. Steam jet ejector systems are commonly employed. Most preferred is to use a Nash-Kinema three-stage vacuum system. Advantageously, the dryer operates at a pressure less than that utilized in prior art drying processes. Reducing pressure allows a given amount of volatile compounds to be removed at a lower temperature and in a shorter period of time. The dryer 22 therefore preferably operates at a temperature of from about 120° F. to about 150° F. and a pressure of from about 2 to about 50 mm Hg. More preferred is to operate dryer 22 at a temperature of from about 120° F. to about 140° F. and at a pressure of from about 5 to about 20 mm Hg. Most preferably, dryer 22 operates at a temperature of from about 120° F. to about 140° F. and a pressure of from about 2 to about 10 mm Hg.

During drying, steam is advantageously contacted with the heated phosphatide concentrate in the dryer 22. The steam has a sufficiently high temperature to vaporize objectionable volatile compounds at the dryer operating pressure. In addition to providing a source of heat, steam also helps carry away the vaporizing objectionable volatile compounds. Preferably, the steam has a temperature of from about 200° F. to about 366° F. and a pressure of about 10 to about 150 psig. Steam is contacted with the heated phosphatide concentrate via a sparging apparatus. Several steam sparging designs are suitable, the most basic of which consists of pipes submerged within the heated phosphatide concentrate and containing drilled holes for admitting steam into the heated phosphatide concentrate. In another suitable sparging configuration, the internal surface area of dryer 22 is perforated by a plurality of holes that allow admitting steam into a thin film of heated phosphatide concentrate traveling along the internal walls of dryer 22. Although the temperature of the admitted steam generally exceeds 150° F., the amount of steam used and the time for which the steam contacts the heated phosphatide concentrate is kept low to ensure that the steam does not increase the temperature of the phosphatide concentrate above about 150° F. Regulating the heated phosphatide concentrate to a temperature of less than about 150° F. minimizes the risk of fixing objectionable volatile compounds onto the lecithin. Because dryer 22 operates at reduced pressure and a temperature of less than about 150° F., it produces dried lecithin by evaporating water. Steam action combines with the action of the evaporating water, providing additional motive force to speed removal of objectionable volatile compounds as they vaporize while the lecithin dries.

The heated phosphatide concentrate remains in contact with steam in dryer 22 for a time sufficient to allow the phosphatide concentrate to be dried down to a lecithin having less than about 0.5 percent by weight water. Most preferably, the lecithin contains no more than about 0.4 percent by weight water. Generally, less than about 1 minute of drying at the operating conditions is required to achieve this amount of moisture reduction. Most preferably, the required minimized level of moisture is reached in less than about 30 seconds. Generally, steam is used in amount of less than about 3 percent by weight based on the weight of the phosphatide concentrate.

The resulting dried lecithin discharges from dryer 22 at a temperature of no more than about 150° F., an important consideration again being to minimize inducing heat damage to the now dried lecithin. Thereafter, the dried lecithin is fed to a cooling unit 24 via pump 23, wherein the dried lecithin is reduced to a temperature of about 110° F. to about 120° F. The cooled dried lecithin is then sent to a storage tank 25.

The lecithin deodorizing process of the invention utilizes greater-than-conventional levels of vacuum and less-than-conventional temperatures. Reducing pressure to levels below those employed in conventional lecithin drying processes allows driving off a greater amount of volatile objectionable compounds at a given operating temperature and residence time. Ensuring that the temperature of the drying lecithin does not exceed 150° F. ensures that the escaping volatiles do not become bound or fixed onto the lecithin. Because operating pressure is kept low, objectionable volatile compounds can be driven off without the need for excessive drying temperatures or residence times.

Vegetable Oil Deodorizing

Figure 3:
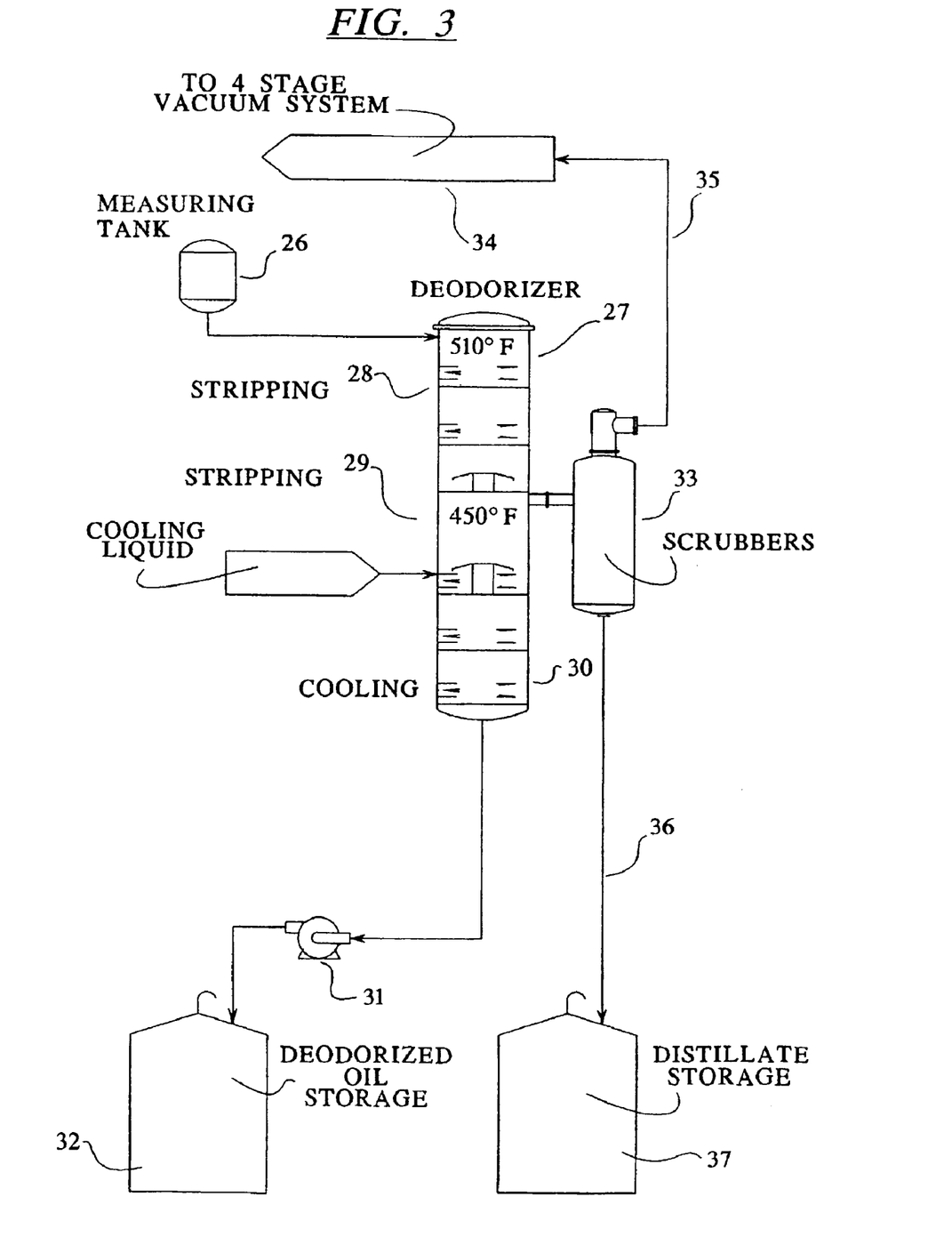
FIG. 3 is a process flow scheme suitable for carrying out the improved vegetable oil deodorizing process of the invention.
Figure 4:
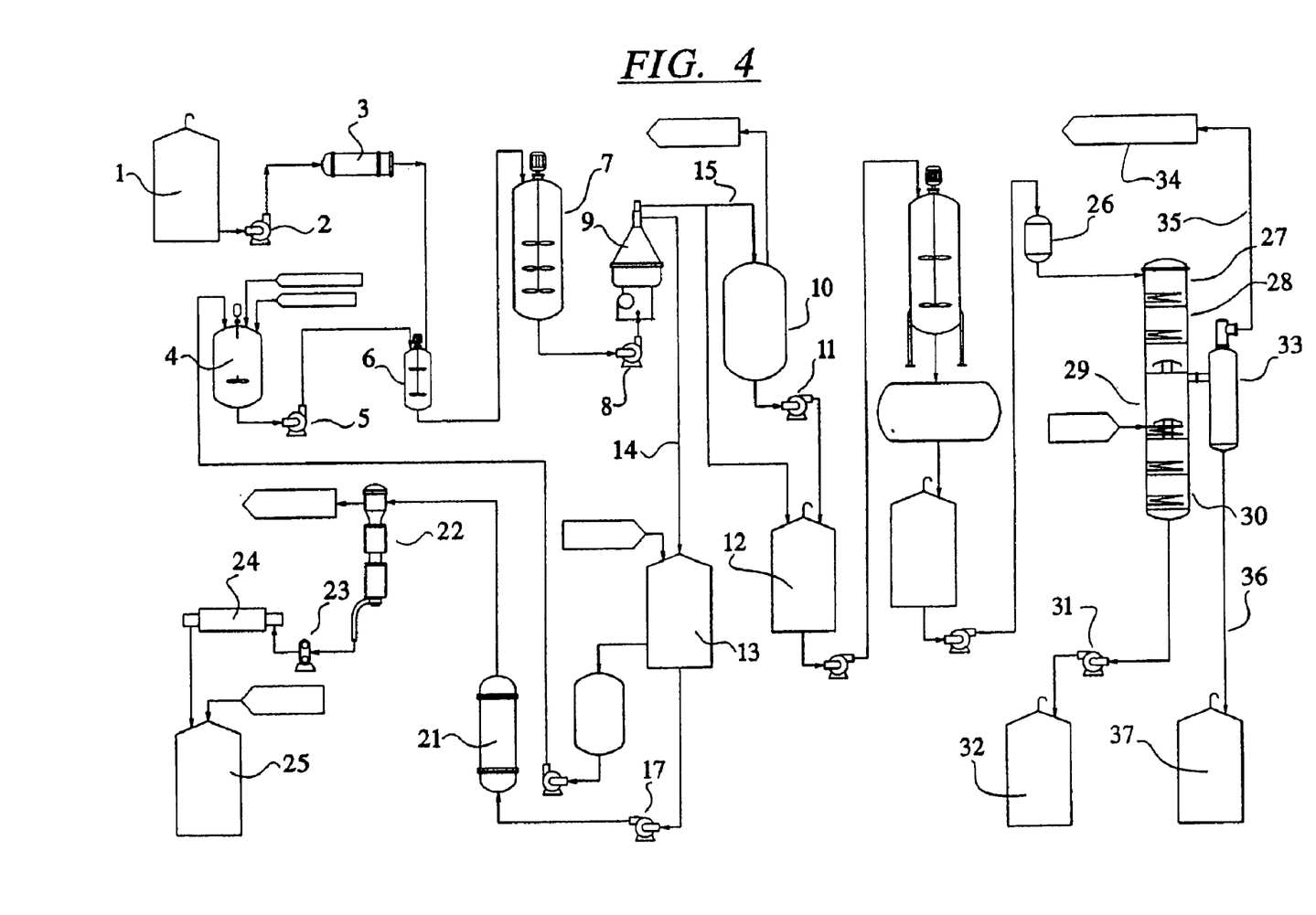
FIG. 4 is a process flow scheme suitable for simultaneously carrying out the improved processes of the invention.

The improved process for deodorizing vegetable oils can be conducted as a batch or continuous process. A continuous process is preferred, however, because it provides uniform temperature gradients and hence leads to greater energy efficiency and lower operating cost. Referring to FIG. 3, vegetable oil is supplied from a measuring tank 26 and fed by gravity to a first tray 28 located within a deodorizer 27 operating at a pressure of less than about 10 mm Hg. First tray 28 operates at a temperature of from about 500° F. to about 525° F. Deodorizer 27 is equipped with at least two trays that are arranged sequentially in any orientation including vertical or horizontal. Preferably, deodorizer 27 is a stripping tower having trays spaced vertically from each other. This preferred arrangement enables using gravity as a motive force to pass oil through deodorizer 27.

The vegetable oil can be supplied at ambient temperature or it can be preheated. Preferably, the vegetable oil is preheated to a temperature near to the operating temperature of first tray 28. The vegetable oil can be preheated either directly, as by mixing with a separate stream of heated oil, or indirectly, as by a convenient means such as a heat exchanger. Suitable vegetable oils include but are not limited to those derived from soybean oil, corn oil, cottonseed oil, palm oil, peanut oil, rapeseed oil, safflower oil, sunflower seed oil, sesame seed oil, rice bran oil, coconut oil, canola oil, and mixtures thereof. A particularly preferred vegetable oil is soybean oil.

The vegetable oil to be deodorized can be either refined or refined and bleached ("RB") oil. Bleaching refers to the process of removing or reducing the levels of pigments, oxidation products, phosphatides, soaps and trace metals. Bleaching also improves the flavor of vegetable oils such as soybean oil. Bleaching is generally characterized as an acid/adsorptive treatment involving moisture, acid, and an absorbent. Bleaching products include neutral earths, acid-activated earths, activated carbon, silicates, and mixtures thereof. Neutral earths, commonly termed natural clays or earths, are hydrated aluminum silicates. Acid-activated clays are bentonites or montmorillonites treated with hydrochloric or sulfuric acid. In bleaching, oil is mixed with an amount of a bleaching product, heated under vacuum to a bleaching temperature, and then filtered.

First tray 28 is equipped with a steam sparging apparatus. Several steam sparging designs are suitable, the most basic of which consists of pipes containing drilled holes for admitting steam into the oil, the pipes being located in the lower part of first tray 28 and evenly spaced across it. The holes are located below the quiescent oil level and face downward to enable intimately mixing steam throughout the oil and to avoid creating any undisturbed zones in the oil. Another suitable sparging design is known as a Votator tray with steam pumps available from DeSmet comprising a central steam-emitting core surrounded by two concentric annular regions separated by an annular wall. A contoured cover is situated above and extends over the steam-emitting core and inner annular region. Steam exits the central steam-emitting core through evenly dispersed holes, all of which are located below the quiescent oil level. The steam intimately mixes with the oil contained in the inner annular region and creates a steam-oil mixture of reduced density. The steam-oil mixture swiftly rises up, strikes the contoured cover, and is deflected out and down in a fine spray pattern onto oil located in the outer annular region. Oil from the outer annular region in turn enters the inner annular region by flowing under the annular wall. This design ensures efficient mixing of steam and oil and produces rapid circulation of oil between the annular regions. Most preferably, first tray 28 is equipped with this sparging design, which achieves swift and very efficient mixing 6f steam and oil.

Steam requirements for vacuum-steam deodorization are generally inversely proportional to the vapor pressure of the objectionable volatile impurities of the oil at the operating temperature. Thus for economical operation, the stripping is carried out at as high a vacuum as practically possible. Steam vaporizes objectionable volatile impurities and carries them away from the oil. In deodorizing at elevated temperature and reduced pressure, steam volume rather than steam weight is important. Thus the amount of steam required depends on the operating pressure and the quality of oil. Generally, steam in an amount of about 0.5 to about 3.0 percent by weight of oil is required at an operating pressure of about 3 mm Hg. At a higher operating pressure of about 6 mm Hg., steam in an amount of about 2 to about 5 percent by weight of oil is generally required. Preferably, first tray 28 operates at a pressure of about 3 mm Hg and employs steam in an amount of about 3 percent by weight of oil.

First tray 28 operates at a temperature of from about 500° F. to about 525° F., preferably from about 505° F. to about 515° F., and most preferably from about 508° F. to about 512° F. Steam contacts the vegetable oil containing objectionable volatile impurities in first tray 28 for a time of less than about 30 minutes, vaporizing a substantial fraction of the objectionable volatile impurities into a first vapor phase, leaving a liquid residue containing a remaining portion of objectionable volatile impurities. An operating temperature of from about 500° F. to about 525° F. is sufficiently high to vaporize tocopherol and other objectionable volatile impurities at the operating pressure. A steam-oil contact time of less than about 30 minutes is long enough to enable removing a significant fraction of tocopherol and other objectionable volatile impurities yet short enough to minimize trans fatty acid formation. Generally, operating first tray 28 at these conditions produces oil having only about 0.7 percent by weight trans fatty acids.

The liquid residue from first tray 28 is fed by gravity to a second tray 29 located within deodorizer 27. Second tray 29 also is equipped with a steam sparging apparatus that can be the same as or different from the steam sparging apparatus in first tray 28. Preferably, second tray 29 is equipped with the same steam sparging apparatus described as being preferred for first tray 28. Second tray 29 operates at a temperature of from about 435° F. to about 465° F., preferably from about 445° F. to about 455° F., and most preferably from about 448° F. to about 452° F. Upon exiting first tray 28, the liquid residue is optionally but preferably cooled to a temperature equal to or near the operating temperature of second tray 29. The liquid residue exiting first tray 28 can be cooled either directly, as by mixing with a separate stream of deodorized oil, or indirectly, as by a convenient means such as a heat exchanger.

Steam contacts the liquid residue in second tray 29 for a time of less than about 30 minutes. An operating temperature of from about 435° F. to about 465° F. is high enough to vaporize a substantial fraction of the remaining portion of objectionable volatile impurities in the liquid residue into a second vapor phase, leaving a deodorized vegetable oil. Because second tray 29 operates at a temperature less than that of first tray 28, the steam-oil contact time in second tray 29 can (but need not) be greater that the steam-oil contact time in first tray 28. Operating second tray 29 at temperature of from about 435° F. to about 465° F. enables removing a significant fraction of the remaining objectionable volatile impurities yet minimizes trans fatty acid formation. Generally, operating second tray 29 at these conditions produces oil having only about 0.9 percent by weight trans fatty acids.

After exiting second tray 29, the deodorized vegetable oil is optionally cooled by cooling apparatus 30. Cooling can be accomplished either directly, as by mixing with a separate stream of cooled deodorized oil, or indirectly, as by a convenient means such as a heat exchanger. The deodorized oil is then sent via pump 31 to a storage vessel 32.

As earlier mentioned, during treatment of the oil in first tray 28, steam vaporizes objectionable volatile impurities and carries them away from the oil and into a first vapor phase. In the same fashion, steam passing through the liquid residue in second stripping tray 29 vaporizes additional objectionable volatile impurities and creates a second vapor phase. The first vapor phase and the second vapor phase are both comprised of water vapor, tocopherols, and other objectionable volatile impurities. The first vapor phase and the second vapor phase are optionally but preferably combined and pulled into a distillate recovery device 33 connected to a vacuum-producing device 34. Vacuum can be generated in vacuum-producing device 34 by any convenient source. Steam ejector systems are commonly employed. Vacuum conditions of six mm Hg or less are readily obtained with three-stage or four-stage steam ejector equipment. Preferably, vacuum-producing device 34 is a four-stage steam ejector system.

Distillate recovery device 33 separates water vapor and air from other condensable vapor components, creating a water vapor/air stream 35 that is then drawn into vacuum-producing device 34. The other condensable vapor components are condensed into a distillate stream 36 in distillate recovery device 33, typically by crossing through a recirculating spray of distillate. Condensed distillate stream 36 is then pumped to a holding vessel 37 for further processing or sale. Distillate recovery device 33 can be of many suitable designs. Preferred is a distillate recovery device 33 comprising a Distillate Scrubber available from DeSmet or Croll-Reynolds.

The improved vegetable oil deodorizing process of the present invention maximizes tocopherol recovery while minimizing trans fatty acid formation. Typically, the present invention allows reducing tocopherol content from a level of about 1400 ppm in the initial feed vegetable oil to a level of about 800 ppm in the final deodorized oil, while maintaining a low trans fatty acid content of about 0.9 percent by weight. Reducing tocopherol to a level below about 600 ppm is generally not warranted because the resultant vegetable oil tends to spoil rapidly. The tocopherol removed from the vegetable oil ultimately is captured into condensed distillate stream 36, which contains about 16 percent by weight tocopherol.

Tocopherol-containing distillates can be profitably sold. Known vegetable oil deodorizing processes generally produce distillate streams in weight amounts of about 0.15 percent by weight of feedstock oil and containing about 14 percent by weight tocopherol. Generally, the process of the invention produces a condensed distillate stream 36 in an amount of about 0.18 percent by weight of feedstock oil and containing about 16 percent by weight tocopherol. Thus, compared to known deodorizing processes, the improved vegetable oil deodorizing process of the invention surprisingly generates significantly more distillate on a weight basis, and the distillate thereby produced has a higher content of tocopherol.

All documents, e.g., patents, journal articles, and textbooks, cited above or below are hereby incorporated by reference in their entirety.

One skilled in the art will recognize that modifications may be made in the present invention without deviating from the spirit or scope of the invention. The invention is illustrated further by the following examples, which are not to be construed as limiting the invention in spirit or scope to the specific procedures or compositions described therein.

EXAMPLE 1

Organic Acid Refining

An aqueous citric acid solution containing 3 percent by weight citric acid based on the combined weight of citric acid and water was admixed with a crude filtered vegetable oil in a ratio of 10:90. The resulting acid-oil blend was mixed in a high shear mixer for 30 seconds to give an acid-and-oil mixture. The acid-and-oil mixture was then transferred to a low shear mixer and mixed for 15 minutes, and then was centifuged to separate the purified vegetable oil phase from the hydrated impurities phase. The resultant purified vegetable oil had the characteristics shown in Table I.

TABLE I

|  | Organic Acid Refined Vegetable Oil of Example 1 ppm | Conventional Water-Degummed Vegetable oil ppm |
|---|---|---|
| Iron | <0.1 | 1.0 |
| Magnesium | <5 | 50 |
| Calcium | <5 | 80 |
| Phosphorous | <10 | 150 |

Table I demonstrates that the organic acid refining process of the present invention effectively removes metal contaminants from crude vegetable oil. Vegetable oil purified by the organic acid refining process contains dramatically lower residual metal levels as compared to vegetable oil obtained via conventional water-degumming. The vegetable oil produced by the invention is unique among vegetable oils because it contains less than about 10 ppm phosphorous and less than about 0.1 ppm iron.

EXAMPLE 2
Organic Acid Refining

The hydrated impurities phase obtained in Example 1 was a hydrolyzed lecithin containing hydratable phosphatides and non-hydratable phosphatides in a ratio of about 9:1. Further analysis produced the results shown in Table II.

TABLE II

| | Hydrolyzed Lecithin Obtained in Example 1 wt % | Normal Lecithin Conventionally Dried wt % |
|---|---|---|
| Phosphatidic acid | 14.18 | 5 |
| Phosphatidyl ethanolamine | 19.91 | 14 |
| Phosphatidyl choline | 14.22 | 16 |
| Phosphatidyl inositol | 8.71 | 9 |
| Lyso or monoacyl forms of glyceryl phospholipids | 6.17 | 0.5 |

Table II demonstrates that the lecithin produced by the organic acid refining process of the invention is a hydrolyzed lecithin because it contains greater than about 5 percent by weight combined lyso and monoacyl forms of glyceryl phospholipids. Surprisingly, the improved lecithin deodorizing process of the invention produces hydrolyzed lecithin directly and simply from a phosphatide-containing vegetable oil without the need for subsequent and expensive processing. Moreover, the hydrolyzed lecithin produced is unique among hydrolyzed lecithins because it contains a ratio of hydratable phosphatides to non-hydratable phosphatides of at least about 9:1.

EXAMPLE 3
Lecithin Deodorizing

A phosphatide concentrate containing about 35 percent by weight water was introduced into a dryer operating at a temperature of 144° F. and a pressure of 5 mm Hg. The phosphatide concentrate was contacted with steam having a temperature of 194° F. and a pressure of 10 psig and used in an amount of 3.0 percent by weight of phosphatide concentrate. The phosphatide concentrate remained in contact with the steam in the dryer for 30 seconds. The resultant deodorized lecithin had the characteristics shown in Table III.

TABLE III

| | Lecithin Deodorized As In Example 3 wt % | Normal Lecithin Conventionally Dried wt % |
|---|---|---|
| Phosphatidic acid | 4.73 | 5 |
| Phosphatidyl ethanolamine | 18.52 | 14 |
| Phosphatidyl choline | 19.93 | 16 |
| Phosphatidyl inositol | 10.90 | 9 |
| Lyso or monoacyl forms of glyceryl phospholipids | 0.22 | 0.5 |

Commercial lecithin, commonly termed normal lecithin, prepared from water-degummed lecithin and dried according to conventional methods generally contains only about 14 percent by weight phosphatidyl ethanolamine and about 16 percent by weight phosphatidyl choline. By contrast, and surprisingly, lecithin deodorized by the process of the present invention generally contains at least about 18 percent by weight phosphatidyl ethanolamine and at least about 19 percent by weight phosphatidyl choline. Thus, the lecithin deodorizing process of the present invention produces little or no reduction in the content of phosphatidyl ethanolamine and phosphatidyl choline. Without wishing to be bound thereby, it is theorized that the process of the invention is non-destructive of phosphatidyl ethanolamine and phosphatidyl choline because it deodorizes lecithin at less-than-conventional temperatures and greater-than-conventional vacuum. Thus, because it contains a relatively higher content of phosphatidyl ethanolamine and phosphatidyl choline as compared to conventional lecithin, lecithin produced according to the invention is unique and possesses unique characteristics, including flavor.

EXAMPLE 4
Lecithin Deodorizing

The flavor of the lecithin obtained from Example 3 was characterized by taste panelists that evaluated flavor type and intensity. The flavor evaluation protocol comprised the steps of:

(1) subjectively ranking the samples in order of ascending odor;

(2) taking into the mouth a small sample of the lecithin having the least odor, holding it for a time of from about 10 to about 20 seconds, and then expelling it;

(3) immediately assigning a numerical score to the intensity of each of several selected flavor types;

(4) allowing the mouth to rest for one minute;

(5) rinsing the mouth with warm water;

(6) cycling through steps (2) to (5) until all samples have been evaluated.

Panelists note whether they detect any of the selected flavor types defined in Table IV, and numerically rank the intensity of any detected flavor according to the corresponding scale also shown in Table IV.

TABLE IV

| | Flavor Intensity | | |
|---|---|---|---|
| Flavor Descriptor | Weak | Moderate | Strong |
| BLAND (a mild and neither irritating nor stimulating flavor) | 10 | 9 | 9 |
| BUTTERY (the flavor of sweet, freshly churned butter) | 9 | 8 | 7 |
| NUTTY (the flavor fresh, sweet nutmeats) | 9 | 8 | 7 |
| BEANY (the flavor of raw beans i.e. fresh raw green beans, soybeans, etc.) | 8 | 7 | 5 |
| GRASSY (reminiscent of freshly cut grass or newly mown hay) | 7 | 6 | 5 |
| RANCID (unpleasant flavor of oxidized fat) | 6 | 4 | 3 |
| METALLIC (sensation produced by puffing in the mouth a silver spoon or a spoon where the silver has worn away to leave the base metal exposed) | 7 | 6 | 4 |

The flavor of the lecithin obtained from Example 3 and of lecithin conventionally dried was characterized by taste panelists with the results shown in Table V.

TABLE V

| | Normal Lecithin Conventionally Dried | | Lecithin Deodorized As In Example 3 | |
|---|---|---|---|---|
| Panelist | Flavor Descriptor | Score/Intensity | Flavor Descriptor | Score/Intensity |
| 1 | GRASSY | 5 = Strong | BUTTERY | 9 = Weak |
| 2 | NUTTY | 7 = Strong | BLAND | 9 = Moderate |
| 3 | BEANY | 5 = Strong | BUTTERY | 9 = Weak |
| 4 | BEANY | 7 = Moderate | BUTTERY | 8 = Moderate |
| 5 | BEANY | 5 = Strong | BUTTERY | 8 = Moderate |
| 6 | BEANY | 5 = Strong | BUTTERY | 8 = Moderate |

Table V demonstrates that panelists characterized the flavor of lecithin deodorized according to the invention as having a predominantly (and desirable) buttery flavor, weak to moderate in intensity. By contrast, panelists characterized the flavor of lecithin conventionally dried as having a predominantly (and undesirable) beany flavor, strong in intensity. Thus, lecithin deodorized according to the present invention has a less intense and more pleasant flavor as compared to lecithin conventionally dried.

As an alternative to conducting taste panel evaluation, flavor profiles can also be conveniently generated and compared via mass spectrograph.

EXAMPLE 5
Vegetable Oil Deodorizing

Refined and bleached vegetable oil was introduced into a deodorizer having two trays, each tray equipped with a steam sparging apparatus. In a first deodorizer configuration, both trays operated at 475° F. In a second configuration, both trays operated at 510° F. In a third deodorizer configuration demonstrating the process of the invention, the first tray operated at 510° F. and the second tray operated at 450° F. In all configurations, the vegetable oil was contacted with steam in each tray for 30 minutes. The resulting products and their characteristics produced are summarized in Table VI.

TABLE VI

| | First Deodorizer Configuration = both trays at 475° F. | Second Deodorizer Configuration = both trays at 510° F. | Third Deodorizer Configuration = first tray at 510° F.; second tray at 475° F. |
|---|---|---|---|
| Tocopherol in feedstock (ppm) | 1263 | 1263 | 1201 |
| Wt % distillate as a percent of feedstock | 0.15 | 0.15 | 0.18 |
| Wt % tocopherol in distillate | 11.17 | 13.19 | 14.5 |
| Wt % trans fatty acid in deodorized oil | 0.6 | 2.1 | 0.8 |
| Tocopherol in deodorized oil (ppm) | 1080 | 721 | 804 |

Conventional vegetable oil deodorizing processes employ either the first or the second deodorizer configuration, depending on whether the goal is to minimize trans fatty acid production or maximize tocopherol recovery. As shown in Table VI, in the first deodorizer configuration—typically employed when seeking minimum trans fatty acid production—uniform and relatively low tray operating temperatures of 475° F. ensures a low trans fatty acid content in the deodorized oil, but undesirably removes only a small amount of tocopherol from the feedstock. In the second deodorizer configuration—typically employed when seeking maximized tocopherol recovery—uniform and relatively high tray operating temperatures of 510° F. allows removing a large fraction of tocopherol from the feedstock but undesirably produces a high trans fatty acid content in the deodorized oil.

By contrast, in the third configuration, illustrating one embodiment of the invention, operating the first tray at 510° F. and the second tray at 475° F. allows removing a large fraction of tocopherol from the feedstock and at the same time ensures a low trans fatty acid content in the deodorized oil. The resulting deodorized vegetable oil is unique among vegetable oils because it contains less than about 0.9 percent by weight trans fatty acid and at the same time less than about 1000 ppm tocopherol.

Additionally, the process of the invention produces more distillate on a weight basis as compared to other conventional deodorizing processes. Moreover, the tocopherol content of the distillate so produced is higher than that of distillates produced using conventional deodorizing methods. Thus, the vegetable oil deodorizing process of the invention generates higher amounts of distillate containing greater amounts of tocopherol as compared to conventional processes. The process of the invention therefore has economic advantages over those previously known because a much greater amount of valuable tocopherol can be removed without inducing undesirable trans fatty acid production.

The invention and the manner and process of making and using it, are now described in such full, clear, concise and exact terms as to enable any person skilled in the art to which it pertains, to make and use the same. Although the foregoing describes preferred embodiments of the present invention, modifications may be made therein without departing from the spirit or scope of the present invention as set forth in the claims. To particularly point out and distinctly claim the subject matter regarded as invention, the following claims conclude this specification.

What we claim is:

1. A process for purifying vegetable oil, comprising:

(a) combining organic acid and vegetable oil to give an acid-oil blend;

(b) mixing the acid-oil blend at high shear for a time sufficient to finely disperse the organic acid in the vegetable oil and give an acid-and-oil mixture; and (c) mixing the acid-and-oil mixture at low shear for a time sufficient to sequester contaminants into a hydrated impurities phase and produce a purified vegetable oil phase.

2. The process according to claim 1, further comprising step (d) separating the hydrated impurities phase and the purified vegetable oil phase.

3. The process according to claim 1, wherein the organic acid is an aqueous organic acid solution.

4. The process according to claim 1, wherein the organic acid is selected from the group consisting of phosphoric acid, acetic acid, citric acid, tartaric acid, succinic acid, and mixtures thereof.

5. The process according to claim 3, wherein the aqueous organic solution is prepared from an organic acid selected from the group consisting of phosphoric acid, acetic acid, citric acid, tartaric acid, succinic acid, and mixtures thereof.

6. The process according to claim 4, wherein the organic acid is citric acid.

7. The process according to claim 5, wherein the aqueous organic acid solution is an aqueous citric acid solution.

8. The process according to claim 1, wherein the vegetable oil is heated to a temperature of from about 190° F. to about 220° F. prior to being contacted with the organic acid.

9. The process according to claim 1, wherein step (b) high shear mixing produces a flow velocity of at least about 45 feet per second.

10. The process according to claim 1, wherein step (b) high shear mixing occurs for a time of less than about 30 seconds.

11. The process according to claim 1, wherein step (c) low shear mixing produces a flow velocity of less than about 20 feet per second.

12. The process according to claim 1, wherein step (c) low shear mixing occurs for a time of less than about 16 minutes.

13. The process according to claim 2, wherein step (d) separating occurs by centrifuging the acid-and-oil mixture.

* * * * *